*(12)* United States Patent
Heide et al.

(10) Patent No.: US 9,107,997 B2
(45) Date of Patent: Aug. 18, 2015

(54) MEDICAL FUNCTIONAL DEVICE, TREATMENT APPARATUS AND METHOD

(75) Inventors: Alexander Heide, Eppstein (DE);
Juergen Klewinghaus, Oberursel (DE);
Robin Partenfelder, Oberursel (DE);
Arne Peters, Bad Homburg (DE);
Christoph Wiktor, Gelnhausen (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 194 days.

(21) Appl. No.: 13/578,301

(22) PCT Filed: Feb. 9, 2011

(86) PCT No.: PCT/EP2011/000599
§ 371 (c)(1),
(2), (4) Date: Oct. 17, 2012

(87) PCT Pub. No.: WO2011/098265
PCT Pub. Date: Aug. 18, 2011

(65) Prior Publication Data
US 2013/0025692 A1 Jan. 31, 2013

(30) Foreign Application Priority Data

Feb. 10, 2010 (DE) .......................... 10 2010 007 464

(51) Int. Cl.
*A61M 1/14* (2006.01)
*A61M 1/10* (2006.01)
*A61M 1/16* (2006.01)
(52) U.S. Cl.
CPC . *A61M 1/16* (2013.01); *A61M 1/10* (2013.01); *A61M 1/106* (2013.01); *A61M 1/1037* (2013.01)

(58) Field of Classification Search
CPC . A61M 1/101; A61M 1/1015; A61M 1/1036; A61M 1/1037; A61M 1/106; A61M 1/1086; A61M 1/3621
USPC ................................................ 604/4.01–6.16
See application file for complete search history.

(56) References Cited

U.S. PATENT DOCUMENTS 4,517,081 A 5/1985 Amiot et al.
5,350,357 A 9/1994 Kamen et al.
(Continued)

FOREIGN PATENT DOCUMENTS

DE 10 2007 010112 A1 9/2008
EP 0 905 379 A1 3/1999
(Continued)

OTHER PUBLICATIONS

PCT International Search Report from PCT/EP2011/000599, mailed on Aug. 11, 2011.
(Continued)

*Primary Examiner* — Philip R Wiest
*Assistant Examiner* — Benjamin Klein
(74) *Attorney, Agent, or Firm* — Kenyon & Kenyon LLP

(57) ABSTRACT

A medical functional device includes at least one first fluid system for receiving at least one medical fluid, at least one first conveying device for conveying the medical fluid, at least one second fluid system for receiving at least one operating fluid, and at least one second conveying device for operating the at least first conveying device, in which the first conveying device is arranged such as to be actuated by means of the operating fluid. A treatment apparatus and a method are also described.

25 Claims, 4 Drawing Sheets

(56) References Cited

U.S. PATENT DOCUMENTS

| | | | |
|---|---|---|---|
| 6,227,820 B1 * | 5/2001 | Jarvik | 417/423.12 |
| 6,439,845 B1 | 8/2002 | Veres | |
| 6,814,547 B2 | 11/2004 | Childers et al. | |
| 2003/0204162 A1 | 10/2003 | Childers et al. | |
| 2004/0019313 A1 | 1/2004 | Childers et al. | |
| 2008/0217245 A1 | 9/2008 | Rambod et al. | |
| 2009/0008331 A1 * | 1/2009 | Wilt et al. | 210/647 |
| 2009/0095679 A1 | 4/2009 | Demers et al. | |
| 2009/0120864 A1 | 5/2009 | Fulkerson et al. | |
| 2009/0299272 A1 | 12/2009 | Hopping et al. | |
| 2012/0265116 A1 * | 10/2012 | Szamosfalvi et al. | 604/6.07 |

FOREIGN PATENT DOCUMENTS

| | | | |
|---|---|---|---|
| JP | 2003 062065 A | 3/2003 | |
| JP | 2004 144070 A | 5/2004 | |
| JP | 2005052240 A | 3/2005 | |
| JP | 2011512882 A | 4/2011 | |
| JP | 2011516227 A | 5/2011 | |
| WO | 2005042065 A1 | 5/2005 | |
| WO | 2009026060 A1 | 2/2009 | |
| WO | 2009/094183 A1 | 7/2009 | |
| WO | 2009/110652 A1 | 9/2009 | |
| WO | 2009/127627 A1 | 10/2009 | |
| WO | 2011/045167 A1 | 4/2011 | |

OTHER PUBLICATIONS

Joutsen K., Wutz Handbuch Wakuumtechnik, Theorie and Praxis, Wiesbaden 2004, pp. 168-185, with English translation of cited sections.

Wikipedia, Dec. 30, 2009—Membranpumpe, with English translation of cited sections.

Wikipedia, Jan. 27, 2010—Hydraulik, with English translation of cited sections.

* cited by examiner

MEDICAL FUNCTIONAL DEVICE, TREATMENT APPARATUS AND METHOD

CROSS REFERENCE TO RELATED APPLICATIONS

The present application is the national stage entry of International Patent Application No. PCT/EP2011/000599, filed on Feb. 9, 2011, and claims priority to Application No. DE 10 2010 007 464.0, filed in the Federal Republic of Germany on Feb. 10, 2010.

FIELD OF INVENTION

The present invention relates to a medical functional device, a treatment apparatus and a method.

BACKGROUND INFORMATION

Medical functional devices are usually provided for fulfilling several functions during a medical treatment. They can be configured or designed, respectively, for receiving medical fluids such as blood and for allowing a through-flow of fluids received therein.

SUMMARY

The medical functional device according to the present invention comprises at least one first fluid system adapted and/or intended for receiving at least one medical fluid, at least one first conveying device for conveying the medical fluid, at least one second fluid system adapted and/or intended for receiving at least one operating fluid or working fluid, respectively, and at least one second conveying device adapted and/or intended for operating the at least first conveying device.

The first conveying device is preferably arranged such that it can be operated, activated or supplied with energy or energized by means of the operating fluid.

In all of the following exemplary embodiments, the use of the expression "may (or can) be" or "may (or can) have" and so on, is to be understood synonymously with "preferably is" or "preferably has", respectively, and so on, and is intended to illustrate certain exemplary embodiments according to the present invention, which are independent from each other.

The medical functional device according to the present invention can be an external or an internal medical functional device. In the context of the present invention, the term "external" describes an element not being present in the treatment apparatus. An example for such an external medical functional device is a disposable blood cassette. In the context of the present invention, the term "internal" describes an element being present in the treatment apparatus, i.e., which is internal or is arranged inside the treatment apparatus, optionally in an exchangeable or replaceable manner, respectively.

The medical functional device according to the present invention can be suited and provided for blood treatment (e.g., hemodialysis, hemofiltration, hemodiafiltration) and for multi-infusion technique. However, it can also be suited and provided for peritoneal dialysis (e.g., automated peritoneal dialysis=APD; APD device).

The term "fluid system" as used herein denotes a system or an arrangement which is suited and provided for receiving fluids.

The fluid system or systems, respectively, are preferably in particular substantially or entirely part of the medical functional device according to the present invention. For example, the fluid systems can be integrally formed or designed, respectively, with the medical functional device or can be integrated into the medical functional device, respectively.

The fluid system or systems, respectively, can comprise or consist of conduits or lines, respectively, tubes, tube systems, channels, valves, restrictors, filters, sensors, chambers, pockets, devices, spaces or areas for accumulating, storing or holding, respectively, or retaining fluids, as well as control devices for controlling a flow passage of the fluids and the like.

The fluid systems can be connected or connectable to a (higher level) fluid circuit. They can form sections or areas of the fluid circuit. The fluid systems can be integrated into the fluid circuit.

According to the present invention, a "first fluid system" is configured and provided for receiving at least one medical fluid and for allowing a through-flow of the fluid received.

The "medical fluid" may be a liquid, a gas, a liquid preparation, a combination or mixture of different liquids and/or gases or the like. The medical fluid can be the peritoneal solution (PD solution) from bags (APD solution bags). This fluid is usually introduced into and removed from the patient's abdomen by one and the same catheter.

In some exemplary embodiments according to the present invention, a medical fluid is provided to get into contact, extracorporeal or intracorporeal, during use of the present invention or a subject-matter according to the present invention, with blood, another component or constituent of the human body, or to mix with it.

According to the present invention, a "second fluid system" is configured and provided for receiving at least one operating fluid or working fluid, respectively, and for allowing a through-flow of the fluid received.

An "operating fluid" or "working fluid" can be a liquid, a gas, a liquid preparation, a combination or a mixture of different liquids and/or gases or the like.

In some exemplary embodiments according to the present invention, both the operating fluid or working fluid and the medical fluid, respectively, are—identical or different—liquids or liquid mixtures. In these exemplary embodiments according to the present invention, the present invention does not relate to a pneumatic system, does not comprise a pneumatic system or is not designed in such way.

The term "conveying device" as used herein denotes a device provided and configured for conveying at least one fluid within a fluid system.

The first and/or the second conveying device are preferably connected with the medical functional device or are designed such as to be connectable thereto or to form an integral part thereof.

The first and/or the second conveying device can each be connected with the medical functional device in a form closure, frictional and/or material connection.

Preferably, the first conveying device and/or the second conveying device are integrated into or formed integrally with the medical functional device.

The first conveying device can be used for conveying medical fluid from an exterior of the medical functional device into an interior of the fluid system or vice versa.

The term "an exterior of the medical functional device" as used herein denotes an area or a section of a fluid circuit, such as of an extracorporeal blood circuit, not forming part of the medical functional device.

The second conveying device can be provided and/or used for conveying operating fluid within the second fluid system and/or for conveying operating fluid from an exterior of the medical functional device into an interior of the second fluid system and/or vice versa. Hereto, the second conveying device can be arranged in or at the second fluid system.

Conveying the operating fluid within the second fluid system can lead to actuating or operating the first conveying device.

The term "actuation" of the first conveying device as used herein denotes the activation or operation, respectively, or control of the first conveying device. This can, for example, include supplying the first conveying device with energy, e.g., flow energy (mechanical power), and/or applying pressure to the first conveying device or the like. For example, the first conveying device can be filled with operating fluid and re-emptied therefrom. The first conveying device can be actuated hydraulically.

The operating fluid can be used for signal, power and/or energy transfer. The medical fluids of the first fluid circuit can be used for signal, power and/or energy transfer as well.

The first conveying device can be actuated by actuating the second conveying device. The actuation of the first conveying device can be effected, activated or induced, respectively, by the action of the second conveying device.

The actuation or control of the first conveying device can merely supportingly or exclusively be effected by actuating the second conveying device.

Together with the (one or more) first conveying device(s) and the (one or more) second conveying device(s), the first fluid system and the second fluid system can form a hydraulic system or a hydraulic circuit.

For several medical liquids or parts of the medical liquids, there can be provided several fluid lines together with respectively several different first conveying devices.

In a preferred exemplary embodiment, at least one first conveying device is arranged such that it is functionally connected or connectable with a pressure side and/or a suction side of the second conveying device.

The first conveying device can be arranged such that it is connected or connectable with a pressure line and/or a suction line of the second fluid system. A line branching from the pressure side and/or from the suction side of the second conveying device to the first conveying device can be placed. The branching line(s) can be connected with or branch from, respectively, the pressure line and/or the suction line of the second fluid system.

During operation of the second conveying device, a pressure difference of the operating fluid between the pressure side and the suction side of the second conveying device can be used for operating the (one or more) first conveying device(s).

The term "at least one first conveying device" or "at least one second conveying device" as used herein means that at least one, however, preferably a plurality or multiplicity of first or second, respectively, conveying devices is provided.

According to the present invention, the following specifications regarding the first conveying device also apply for the second conveying device.

The first conveying devices can be similar or of the same or identical type, respectively. They can be identical in construction.

The first conveying devices can be different from each other.

The first conveying devices can be operated according to different functional or operational modes or modes of action.

A plurality or multiplicity of first conveying devices can be congenial or similar, respectively, or of a first type, respectively. Another plurality or multiplicity of first conveying devices can be designed as conveying devices of one or several other types.

The first conveying devices can be controlled by means of suited control devices. A plurality or multiplicity of such control devices can be provided.

The first conveying devices can be controlled or regulated, respectively, together or by only one control device, respectively.

Each first conveying device can be controlled by another (separate) control device.

The first conveying devices can be controlled by several and/or different control devices according to, for example, different modes of action.

One part of the first conveying devices can be controlled concertedly, and another part can be controlled separately.

The first conveying devices can be controlled such that they can convey simultaneously and/or to the same extent, not simultaneously and/or to a different extent, or even not at all.

Suitable control devices include valves or valve devices, respectively, through-flow control devices, devices for effecting or supporting the inflow or outflow of fluids such as nozzles, venturi-nozzles, grommets, ports, lugs, through-flow locking devices such as clamps, stop valves, baffles, devices for regulating or changing the flow or the flow rate, respectively, such as flow rapids and the like.

The first conveying devices can all be arranged within the same fluid system.

The first conveying devices can be provided in sections or areas of a (higher level) first fluid system of the medical functional device. They can be arranged in co-ordinate fluid systems and/or in branches or bifurcations, respectively, of the first fluid system.

The first conveying devices can each be arranged in a separate fluid system, i.e., in a particular fluid system for each conveying device.

Single fluid systems may be separated spatially and/or functionally.

The first conveying devices can convey same or identical fluids. They can convey different fluids. The fluids conveyed by the first conveying devices may each be medical fluids, respectively. However, a part of the first conveying devices can also convey non-medical fluids.

In preferred exemplary embodiments, first conveying devices are arranged such that they are functionally connected or connectable with the pressure side and/or the suction side of the second conveying device or between the pressure side and the suction side in parallel and/or in series connection.

FIG. 1 exemplarily shows such an arrangement.

In another preferred exemplary embodiment, the first conveying device is a displacement pump.

Suitable displacement pumps include, e.g., membrane pumps, piston pumps, flexible tube pumps, and peristaltic pumps.

Membrane pumps can comprise a chamber for conveying the medical fluids which are separated from the operating fluid of a pump membrane. The operating fluid serves for displacing the membrane in order to effect a pump action.

In another preferred exemplary embodiment, the second conveying device is a centrifugal pump or a rotary pump.

The centrifugal pump or rotary pump can advantageously be designed such that it provides a high volume flow at low pressures, a low volume flow at high pressure, and/or a high pressure without any volume flow. Thereby, the pressure difference depends on the revolutions per minute.

The maximal pressure of a centrifugal pump can be set via the revolutions per minute such that the maximal pressure load on the entire hydraulic system can advantageously be defined (very) properly or exactly.

In another preferred exemplary embodiment, the second conveying device comprises at least one rotating or rotational section, respectively, for conveying the operating fluid.

The rotational section can exclusively or completely, respectively, or additionally be supported or mounted magnetically. The support or bearing can completely or additionally be effected by an axis. The kind of support or bearing can be independent from the kind of transfer of input power.

The rotational section can be arranged inside or in an interior of, respectively, the second conveying device.

The rotational section may be an impeller.

The second conveying device may be an impeller pump.

In another preferred exemplary embodiment, the rotational section is configured such as to be operated magnetically by an external actuation. Alternatively, the actuation could also be mechanically, e.g., by a driveshaft.

The term "external actuation" as used herein denotes an actuation of the rotational section which does not form a part of the medical functional device.

The external actuation can be arranged at an apparatus. The external actuation can form a part of such an apparatus.

The apparatus can be provided and configured such as to be functionally coupled to the medical functional device according to the present invention.

The magnetic power or action of actuation can be effected by magnets. It can be effected by current-carrying conductors. For example, current-carrying coils can be used.

The second conveying device can be a magnetically supported centrifugal pump which is commercially available.

Such a magnetically supported centrifugal pump can have the advantage that a mechanical and/or electrical interface to the machine or the treatment apparatus, respectively, is not required and/or fluids do not have to be transferred from the machine to the pump. This can allow for a particular cost-efficient production of the functional device according to the present invention. Furthermore, this can reduce the potential contamination risk accompanying such interfaces.

In another preferred exemplary embodiment, the first fluid system and the second fluid system are separated from each other in a fluid-tight manner.

The first fluid system and the second fluid system can substantially or completely be separated from each other in a fluid-tight manner.

The term "fluid-tight" as used herein describes a state in which a transition or transfer of fluids between the first fluid system and the second fluid system is substantially or completely excluded.

This can mean that no operating fluid can get from the second fluid system into the first fluid system. It can also mean that no medical fluid can get from the first fluid system into the second fluid system.

The first fluid system and/or the second fluid system can be self-contained fluid systems.

This can offer the advantage that a mixing of operating fluid with medical fluid can substantially or completely be avoided. A potential contamination risk for the medical fluids to be treated can thus advantageously be reduced or excluded.

The medical fluids can, for example, be blood, dialysis liquid, substitute liquid, drugs, drug preparations, as well as mixtures or combinations thereof.

A "drug preparation" as used herein can be understood as a solution, suspension, emulsion, extract and the like of drugs in combination with appropriate solvents, excipients and the like.

Drugs include, e.g., anticoagulants such as heparin and citrate, as well as coagulants such as calcium, for example, a Ci-Ca anticoagulation and the same. It can be envisaged to infuse the drugs into the extracorporeal blood circuit.

The operating fluid can be selected from dialyzing liquid, substituate liquid, sterile compressed air, oil, hydraulic oil, water, purified water (permeate) from a reverse-osmosis system or source (RO system) or another liquid, as well as mixtures and combinations thereof.

The substituate liquid can be sterile. The substituate liquid can be an isotonic saline solution such as, e.g., 0.9% NaCl solution.

In case, the dialyzing liquid and/or the substituate liquid are used both as medical fluid and as operating fluid, they can be taken from the same source. For this purpose, the dialyzing liquid and/or the substituate liquid can continuously be circulated from the same supply. However, it is likewise possible to branch off a part of the dialyzing liquid and/or the substituate liquid from the supply and to use it merely for actuating the first conveying devices (i.e., for "generating energy").

The use of dialyzing liquid and/or substituate liquid as operating fluid can advantageously contribute to increase the safety of the hydraulic actuation system of the medical functional device according to the present invention.

Thus, for example, even in case of a fault which can intrinsically be excluded, a contamination of the medical fluid to be treated can advantageously be prevented.

In another preferred exemplary embodiment, the medical functional device is designed as a disposable cassette and/or as a tube set.

The term "disposable cassette" as used herein denotes a device which is—for example, in the field of medicine or medicine technology—designed or used as a single-use or disposable article.

The medical functional device can be designed as a disposable cassette for extracorporeal blood treatment, in particular as a blood cassette, forming a part of an extracorporeal blood circuit, and/or as a dialysate cassette forming a part of a dialysate circuit or being provided for forming a part of a dialysate circuit during its normal use.

The disposable cassette can completely or partly consist of a rigid part. It can be manufactured from a plastic or synthetic material. The disposable cassette can be produced by using an injection molding process.

Components of the cassette such as fluid systems, e.g., conduits or lines, respectively, channels, chambers, valves, throttles and the like, can be formed during manufacture of the disposable cassette. Other components of the cassette such as, for example, first and/or second conveying devices can be integrally formed with the disposable cassette during manufacture thereof and/or can be connected with the disposable cassette during or after manufacture thereof in a form closure, frictional and/or material connection.

An object of the present invention is further solved by a treatment apparatus, in which all advantages achievable by the medical functional device according to the present invention can likewise undiminishedly or without detriment to the function be obtained with the treatment apparatus according to the present invention.

The treatment apparatus according to the present invention is suited for treating medical fluids. It comprises at least one control device which is provided and/or configured such as to operate at least one second conveying device of a medical functional device. In some exemplary embodiments according to the present invention, the control device is provided and/or configured such as to control valves in the first and/or in the second fluid system by appropriate actuators.

The control device can be computer-based. It can be or comprise a micro-processor.

In a preferred exemplary embodiment, the treatment apparatus comprises a device which is provided and configured such as to operate the second conveying device by a magnetic actuation interface.

Such a device can produce or effect a magnetic action or force which can be used for operating the second conveying device or parts or sections thereof, respectively. The device can in particular be provided to act on the rotational section of the conveying device such as an impeller.

The device can, for example, be designed as a magnet or a magnetically acting system and/or as (one or more) current-carrying conductor(s) such as, for example, one or more current-carrying coils.

Furthermore, the treatment apparatus can comprise additional interfaces. Such additional interfaces can also be provided for operating the second conveying device or parts or sections thereof, respectively. They can also be provided and configured for controlling or actuating control devices for controlling the first conveying devices.

The treatment apparatus can be functionally couplable or connectable with, adapted for coupling or connecting with or comprise a medical functional device, in particular a medical functional device according to the present invention.

In order to perform a medical treatment, the treatment apparatus can further be couplable or connectable with, adapted for coupling or connecting with or comprise additional devices such as, for example, an extracorporeal blood circuit, control devices for controlling the performance of a medical treatment, devices for displaying or representing states or conditions, respectively, and/or parameters of the medical treatment such as displays and the like, devices for operating, actuating or controlling one or more components of the treatment apparatus, such as keyboards and the like, in order to induce or effect, respectively, the performance of a medical treatment, and the like.

In some exemplary embodiments, the treatment apparatus comprises an even or uneven coupling surface which is an interface between the medical functional device and the treatment apparatus. The coupling surface can comprise actuators (e.g., for actuating valves), sensors (e.g., pressure sensors) and coupling elements (e.g., push-in elements).

The treatment apparatus can, for example, be a blood treatment apparatus, a multi-infusion apparatus, a peritoneal dialysis apparatus or an infusion apparatus.

An object of the present invention is further solved by a method, in which all advantages achievable with the medical functional device can likewise undiminishedly or without detriment to the function be obtained with the method according to the present invention.

The method according to the present invention comprises conveying at least one medical fluid by using at least one medical functional device according to the present invention or at least one treatment apparatus according to the present invention.

In some exemplary embodiments, the method according to the present invention comprises of one or more of the above mentioned process steps or activities, which can also be read from the previously discussed.

In a preferred exemplary embodiment, the method according to the present invention comprises operating at least one second conveying device for conveying at least one operating fluid within a second fluid system in order to operate a first conveying device for conveying a medical fluid.

The method according to the present invention can comprise controlling a multiplicity of control devices in order to separately control a multiplicity of first conveying devices in series connection or in parallel.

In some exemplary embodiments, the method according to the present invention comprises simultaneously operating at least one blood pump and at least one dialysate pump in a controlled manner (wherein, also in the following, the pumps are to be understood as first conveying devices).

In some exemplary embodiments according to the present invention, the method comprises simultaneously operating at least one pump for heparin or a heparin-containing solution in a controlled manner.

In some exemplary embodiments according to the present invention, the method comprises simultaneously operating at least one pump for citrate-containing solution and/or at least one further pump for a calcium-containing solution in a controlled manner.

In some exemplary embodiments according to the present invention, the method comprises simultaneously operating at least one substituate pump in a controlled manner.

In some exemplary embodiments according to the present invention, the method comprises simultaneously operating at least one predilution pump and/or at least one postdilution pump in a controlled manner.

In some exemplary embodiments according to the present invention, the method comprises simultaneously operating at least one pump for the infusion of a drug into the extracorporeal blood circuit in a controlled manner.

In some exemplary embodiments according to the present invention, the method comprises controlling at least one valve in the operating fluid lines on the inlet and/or the outlet sides of the pumps.

The present invention provides a medical functional device, for example, in form of a single-use cassette. Due to its design according to the present invention, the cassette can advantageously have a particular high integration level.

The medical functional device according to the present invention can advantageously be a self-sufficient unit or self-sufficient system, respectively. By operating the first conveying devices by the operating fluid conveyed by the second conveying device, the medical functional device can advantageously generate the energy required for operating all first conveying devices and optionally additional conveying devices used for the medical treatment, such as, for example, a blood pump and/or a conveying device of a balancing chamber, by itself.

As the medical fluid to be treated or applied is not directly in fluid or operative connection or communication, respectively, with the treatment apparatus, a contamination risk of the medical fluids to be treated or applied can advantageously be reduced. The medical functional device of the present invention can be a hermetically sealed disposable cassette. In this way, it can advantageously offer a high protection for the medical fluids to be treated or applied.

As both the first conveying devices and the second conveying device are integrated into the medical functional device, it can advantageously be possible to provide a simplified hygiene concept for the use of the medical functional device. As the medical functional device according to the present invention with all its components can be designed as a single-use article or disposable, respectively, cleaning and/or sterilization of single implement parts or elements of the medical functional device according to the present invention can be omitted. For this reason, the medical functional device according to the present invention as a whole can advantageously provide a cost-efficient device for medical treatment methods.

As, in such a medical functional device, all elements or components which come in fluid contact are disposed of after one single use of the medical functional device according to the present invention, the safety and hygiene of the medical treatment method can advantageously be further improved.

The magnetic actuation interface for operating the second conveying device or a rotational section thereof, respectively, can advantageously provide a contactless and/or sealing-free operation of the second conveying device. In this way, it can advantageously be possible to waive open interfaces between the medical functional device and the treatment apparatus.

This way, it can advantageously be possible to ensure a particular safe operation of the medical functional device. A contamination risk of the operating fluid can thus advantageously be reduced and even completely excluded.

In the medical functional device according to the present invention, it can be advantageously possible to transfer the required operation energy for a plurality of first conveying devices via only one single (contactless) interface to the disposable cassette and to distribute it there onto the plurality of first conveying devices by the pressure increase or alteration. In this way, it is advantageously possible to waive a multiplicity of individual actuation devices at the machine's side for a plurality of first conveying devices. The medical functional device according to the present invention can thus advantageously provide a very simple, cost-efficient and/or safe actuation concept.

As there is only one actuation interface required between the medical functional device and the treatment apparatus, the treatment apparatus according to the present invention can advantageously comprise a correspondingly simple and technically uncomplicated machine surface.

The machine surface can advantageously be designable in a free manner. The machine surface can advantageously be easy to clean. An air connection and/or rotor axes for peristaltic pumps can advantageously be waived.

As the first functional devices in the medical functional device according to the present invention do not have to be operated singularly, for example, via a connection to an external apparatus such as a treatment apparatus, it can advantageously be possible to reduce technical complexity as compared to the use of, e.g., pneumatically operated membrane pumps as first conveying devices.

Moreover, it can advantageously be possible to dispense with a powerful compressor for operating pneumatic membrane pumps for advancing or conveying, respectively, blood or dialysate. This can advantageously contribute to minimizing the development of what could be a high noise source.

Additionally, by using dialyzing fluid and/or substituate fluid as operating fluid, it can advantageously be possible to waive preparation of any further fluid for use as a sterile operating fluid, such as, for example, sterilized air. According to prior art, dialyzing fluid and/or substituate fluid can be produced and/or prepared online in the treatment apparatus.

An "open" interface to the environment for, e.g., sucking air, can thus further advantageously be omitted. In this way, it can advantageously be possible to reduce the effort for ensuring safety and hygiene.

As non-compressible fluids are preferably used as flowing media, it can further advantageously be possible to reduce flow noises.

Exemplary embodiments of the present invention are described herein with reference to the accompanying drawings.

DETAILED DESCRIPTION

Figure 1:
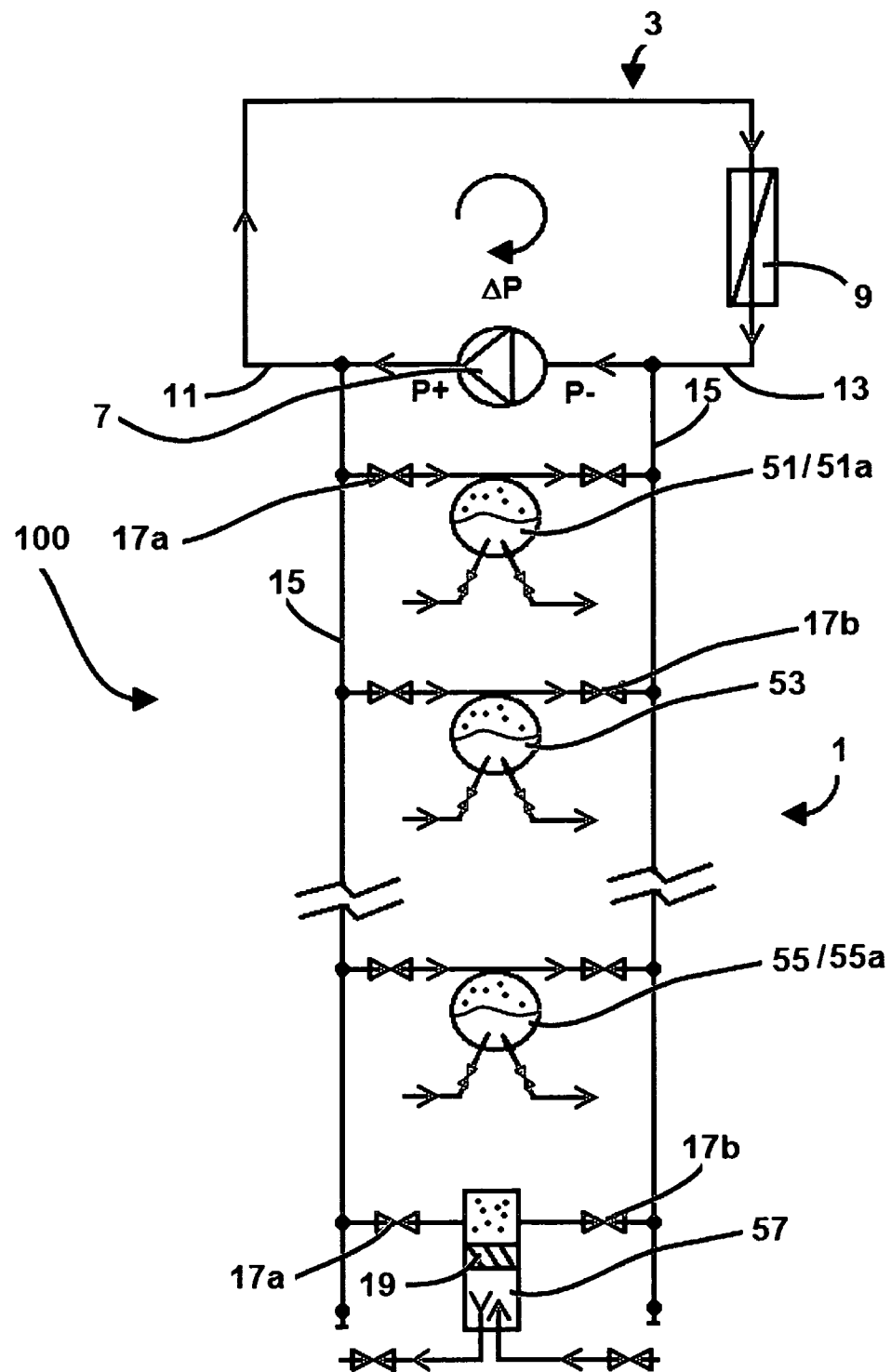
FIG. 1 shows an arrangement of a hydraulic system of a medical functional device according to an exemplary embodiment of the present invention in a schematically simplified manner.

FIG. 1 shows a hydraulic system 100 in an external medical functional device as an exemplary embodiment for a medical functional device. The external medical functional device can be a blood cassette, which is assumed in the following. However, the external medical functional device can also be something other than a blood cassette.

The hydraulic system 100 comprises a first fluid system 1 and a second fluid system 3.

The first fluid system 1 comprises a multiplicity of first conveying devices 51 (or 51a), 53, 55 (or 55a) and 57. Those are merely exemplarily designed or illustrated, respectively, as membrane pumps 51, 53 and 55 and as a piston pump 57.

The second fluid system 3 comprises a second conveying device 7. The second conveying device 7 can be a centrifugal pump. An impeller being magnetically supported within the closed cassette and being magnetically actuated from outside of the cassette can preferably be integrated in the external medical functional device, i.e., cassette-integrated. It can be actuated at the machine side from a coupling surface or plane of the treatment apparatus. The actuation can preferably be contactless.

The second conveying device 7 conveys the operating fluid in a first conveying direction. In FIG. 1, the first conveying direction of the operating fluid which is effected clockwise is indicated by the three-quarter circle shaped arrow and the arrowheads drawn in the second fluid system 3.

As shown in FIG. 1, a filter 9 or a throttle is arranged in the second fluid system 3.

The second fluid system 3 comprises a pressure line 11 which is arranged at a pressure side P+ of the second conveying device 7.

The second fluid system 3 comprises a suction line 13 which is arranged at a suction side P− of the second conveying device 7.

In FIG. 1, four first conveying devices are exemplarily shown. The first conveying devices can be connected between the pressure side P+ and the suction side P− of the second conveying device 7. As shown in FIG. 1, the first conveying devices are connected to the pressure line 11 and the suction line 13 via branching lines 15. The first conveying devices 51 (or 51a), 53, 55 (or 55a) and 57 are here connected with the pressure side P+ and the suction side P− of the second conveying device 7 in parallel.

The first conveying devices 51 (or 51a), 53, 55 (or 55a) and 57 convey the (one or more) medical fluids in a direction opposite to the first conveying direction of the operating fluid, i.e., counter-clockwise in FIG. 1, as is indicated by the arrowheads shown in FIG. 1.

In the hydraulic system 100 as shown in FIG. 1, in principle every pump requiring a pressure difference ΔP for operation can be used as first conveying device. If, for example, membrane pumps are used as first conveying devices 51, 51a, 53, 55 and 55a, the respective operating fluid chambers of the membrane pumps 51, 51a, 53, 55 and 55a can be filled via the pressure line 11 of the second conveying device 7 during operation. By switching the respective valves 17a on the input side and 17b on the output side, the operating fluid chambers of the membrane pumps 51, 51a, 53, 55 and 55a can be emptied again.

In an extracorporeal blood treatment with a citrate anticoagulation (Ci-Ca anticoagulation), at least one membrane pump 51 for conveying a citrate-containing solution and concurrently at least one further independent membrane pump 51a for conveying a calcium-containing solution are operated. The membrane pump 53 can, for example, serve for conveying heparin. The membrane pump 55 can, for example, serve for conveying blood. The membrane pump 55a can, for example, serve for conveying dialysate. All of the pumps 51, 51a, 53, 55 and 55a mentioned-above can be operated simultaneously. They are connected in parallel. However, some of them could also be connected in series. The same also applies for additional pumps or membrane pumps not shown or mentioned here.

Also, a piston pump can be used, which is in FIG. 1 shown as a piston pump 57. In this case, an overpressure can be directed to an actuation piston 19 of the piston pump 57 by respective valves. Other than during operation of a membrane pump, the pump lifts of the piston pump 57 can exclusively be actuated by the overpressure from the pressure line 11.

As indicated with the breaks in lines 15 respectively between the membrane pump 53 and the membrane pump 55, an arbitrary additional number of first conveying devices can be arranged in the first fluid system 1. When the second conveying device 7 conveys in the closed second fluid system 3, the pressure can rise in a manner dependent on the rotational speed and cause the fluid in the pump housing to flow out. If the second conveying device 7 delivers in a circuit, then respectively high pressures (up to ca. 2 bar) at the pressure side P+ and low pressures (up to ca. −800 mbar) at the suction side P− can result. Volume flows of up to 22 l/min can result therefrom.

In order to retain low pressure for emptying the first conveying devices sufficiently, several venturi-nozzles (not shown in FIG. 1) can be connected or integrated into the hydraulic system 100.

Figure 2:
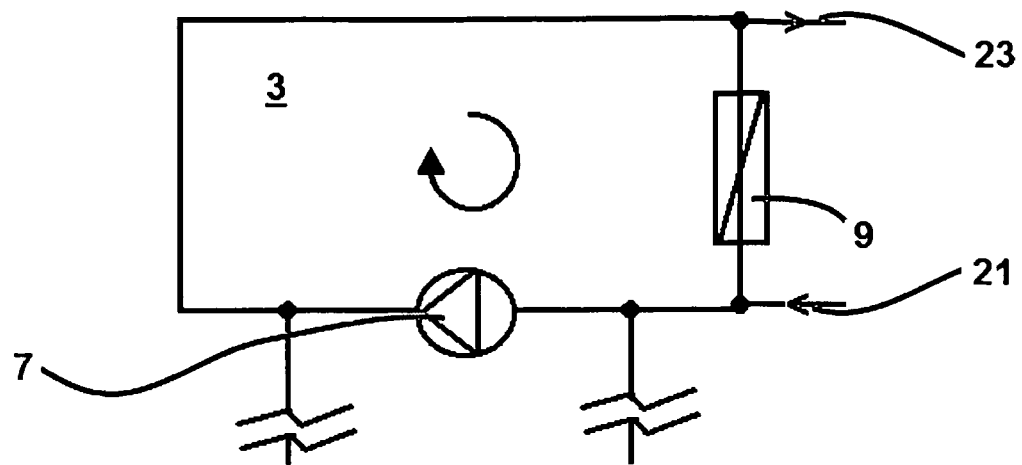
FIG. 2 shows a segment of the arrangement of FIG. 1 comprising a feed or discharge line, respectively, for an operating fluid.

FIG. 2 shows a segment of the arrangement as shown in FIG. 1 in a modification hereof according to the present invention.

The second fluid system 3 shown in FIG. 2 comprises a feed line 21 and a discharge line 23 for operating fluid before or after, respectively, filter 9 (as in FIG. 1, this can also be a throttle, a restrictor or the like).

Figure 3:
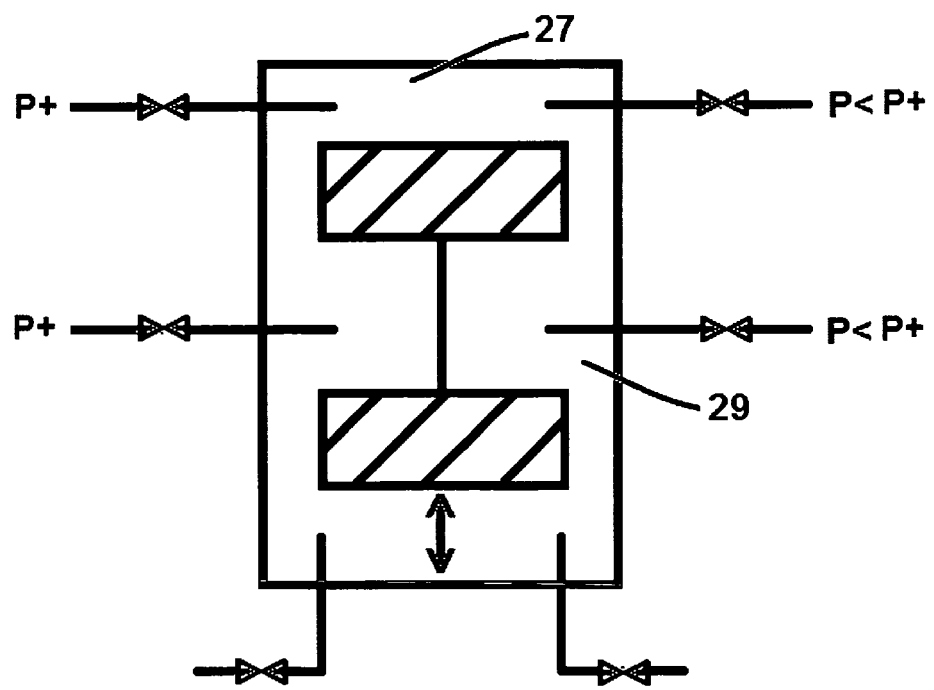
FIG. 3 shows a double piston pump having a second working space.

FIG. 3 shows a double piston pump 25 comprising a first working space 27 and a second working space 29, in particular for being used as a pump 19 in the first fluid system 1.

Figure 4:
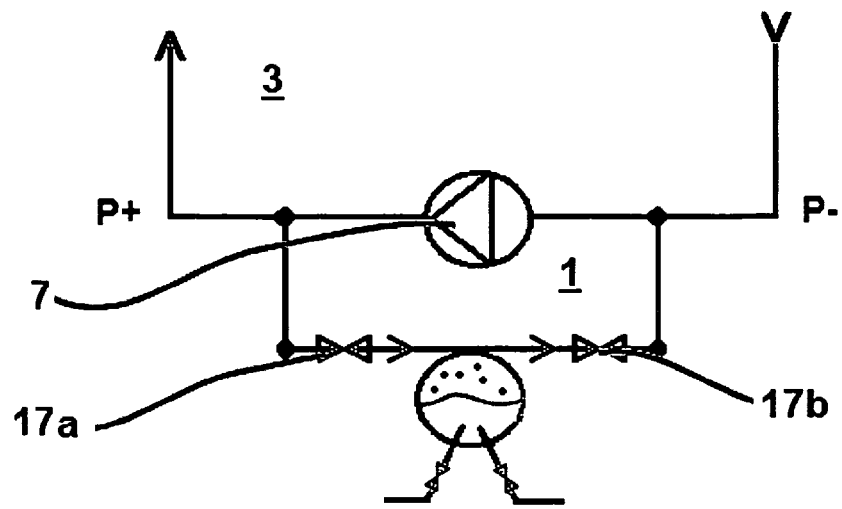
FIG. 4 shows a flow diagram presenting a modified valve equipment.

FIG. 4 shows a flow diagram presenting a modified valve configuration of the medical functional device according to the present invention.

Figure 5:
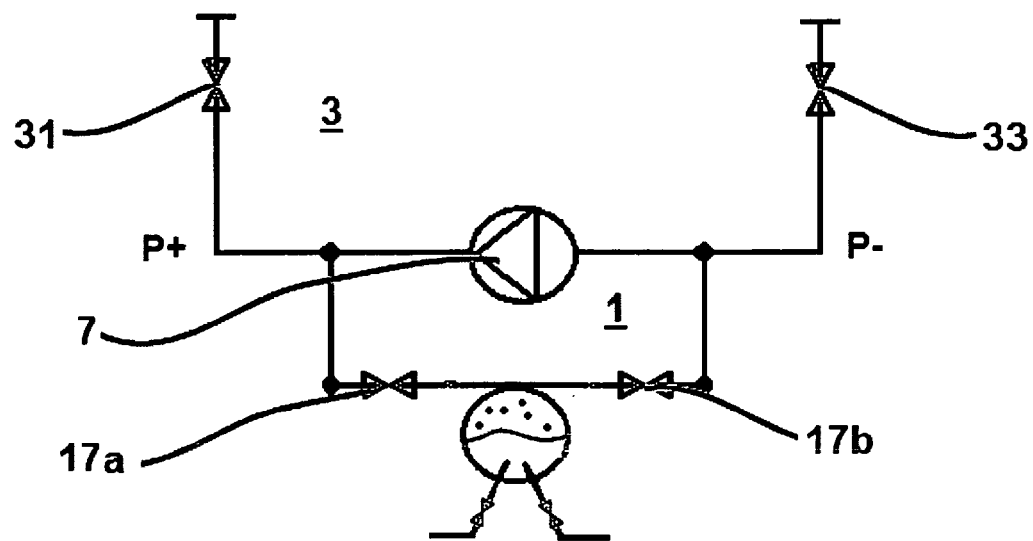
FIG. 5 shows another flow diagram presenting a modified valve equipment.

FIG. 5 shows another flow diagram presenting a modified valve equipment; in comparison to the arrangement of FIG. 4, additional valves 31 and 33 are shown in FIG. 5.

Figure 6:
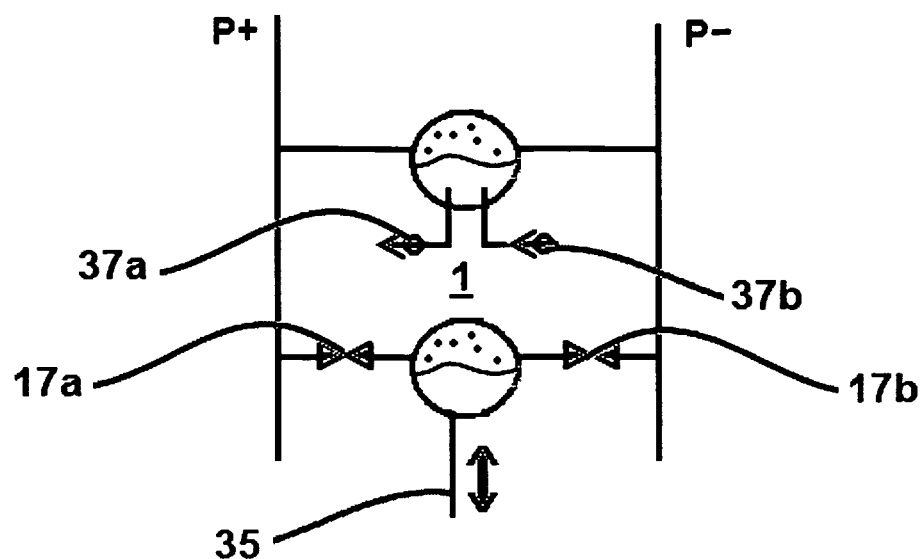
FIG. 6 shows a segment of the representation of FIG. 1 comprising a single line.

FIG. 6 shows a segment of the representation of FIG. 1 comprising a single line 35 with which a medical fluid can be sucked and pumped back again via a branch line as envisaged in a special exemplary embodiment also comprised by the present invention. This branch line or single line, respectively, can be used for sampling, batch conveyance, single needle hemodialysis, peritoneal dialysis cycler, etc.

Furthermore, passive non-return valves 37a and 37b are shown in FIG. 6. Each of the valves mentioned above in an arbitrary context can of course be designed as such a return valve 37a or 37b as is easily recognized by a person skilled in the art.

The invention claimed is:

1. A medical functional device, comprising
at least one first fluid system configured for receiving at least one medical fluid;
at least one first conveying device configured for conveying the at least one medical fluid;
at least one second fluid system configured for receiving at least one operating fluid; and
at least one second conveying device configured for operating the at least one first conveying device;
wherein the at least one first conveying device is arranged such as to be actuated by the at least one operating fluid,
wherein the medical functional device is configured as at least one of a disposable cassette, a blood cassette, a dialysate cassette for extracorporeal blood treatment, or a cassette for peritoneal dialysis,
wherein the at least one second conveying device is a centrifugal pump.

2. The medical functional device according to claim 1, wherein the at least one first conveying device is arranged such that it is one of connected or connectable with at least one of a pressure side or a suction side of the second conveying device.

3. The medical functional device according to claim 2, wherein a plurality of the at least one first conveying device are arranged such that they are functionally one of connected or connectable in parallel with at least one of the pressure side or the suction side of the second conveying device.

4. The medical functional device according to claim 2, wherein a plurality of the at least one first conveying device are arranged such that they are functionally one of connected or connectable in series connection with at least one of the pressure side or the suction side of the second conveying device.

5. The medical functional device according to claim 1, wherein the first conveying device is a displacement pump which is selected from the group consisting of membrane pumps, piston pumps, flexible tube pumps and peristaltic pumps.

6. The medical functional device according to claim 1, wherein the second conveying device comprises at least one rotational section which is supported magnetically.

7. The medical functional device according to claim 6, wherein the rotational section is configured such as to be operated magnetically by external actuation.

8. The medical functional device according to claim 1, wherein the first fluid system and the second fluid system are separated from each other in a fluid-tight manner.

9. The medical functional device according to claim 1, wherein the medical fluid includes at least one of blood, dialyzing liquid, substitute liquid, drugs, or drug preparations.

10. The medical functional device according claim 1, wherein the operating fluid includes at least one of dialyzing liquid, substituate liquid, sterile compressed air, hydraulic oil, or water.

11. The medical functional device according to claim 1, wherein the at least one second conveying device is part of or integrated into the medical functional device.

12. The medical functional device according to claim 1, wherein the at least one second conveying device is arranged inside the medical functional device.

13. A treatment apparatus for treating medical fluids, comprising:
at least one control device configured to operate the at least one second conveying device of the medical functional device according to claim 1.

14. The treatment apparatus according to claim 13, wherein the control device is configured to operate the second conveying device by a magnetic actuation interface.

15. The treatment apparatus according to claim 13, wherein the apparatus is one of functionally couplable with or further comprises the medical functional device according to claim 1.

16. The treatment apparatus according to claim 13, wherein the apparatus is one of a blood treatment apparatus or an infusion apparatus.

17. A method for conveying at least one medical fluid, comprising:
using one of (a) at least one medical functional device according to claim 1 or (b) at least one treatment apparatus according to claim 13.

18. The method according to claim 17, further comprising:
operating the at least one second conveying device configured for conveying the at least one operating fluid within the second fluid system in order to operate the first conveying device for conveying the medical fluid.

19. The method according to claim 17, further comprising:
simultaneously operating at least one blood pump and at least one dialysate pump in a controlled manner.

20. The method according to claim 17, further comprising:
simultaneously operating one of (a) at least one heparin pump or (b) a heparin-containing solution pump in a controlled manner.

21. The method according to claim 17, further comprising:
simultaneously operating at least one citrate-containing solution pump and at least one further calcium-containing solution pump in a controlled manner.

22. The method according to claim 17, further comprising:
simultaneously operating at least one substituate pump in a controlled manner.

23. The method according to claim 17, further comprising:
simultaneously operating at least one of (a) at least one predilution pump or (b) at least one postdilution pump in a controlled manner.

24. The method according to claim 17, further comprising:
simultaneously operating at least one pump for infusion of a drug into an extracorporeal blood circuit in a controlled manner.

25. The method according to claim 17, further comprising:
controlling at least one valve in operating fluid lines on at least one of inlet or outlet sides of the at least one first conveying device.

* * * * *